(12) United States Patent
Patel

(10) Patent No.: US 12,329,671 B2
(45) Date of Patent: Jun. 17, 2025

(54) POSTURE CORRECTION BRACE

(71) Applicant: Veeral Mansukhlal Patel, Jamnagar (IN)

(72) Inventor: Veeral Mansukhlal Patel, Jamnagar (IN)

(*) Notice: Subject to any disclaimer, the term of this patent is extended or adjusted under 35 U.S.C. 154(b) by 789 days.

(21) Appl. No.: 17/497,999

(22) Filed: Oct. 11, 2021

(65) Prior Publication Data
US 2022/0142804 A1 May 12, 2022

Related U.S. Application Data

(60) Provisional application No. 63/134,192, filed on Jan. 6, 2021.

(51) Int. Cl.
*A61F 5/02* (2006.01)

(52) U.S. Cl.
CPC ................... *A61F 5/026* (2013.01)

(58) Field of Classification Search
CPC ........ A61F 5/026; A61F 5/0118; A61F 5/028; A61H 39/04; A41F 19/00
USPC ............................................. 602/19; 128/845
See application file for complete search history.

(56) References Cited

U.S. PATENT DOCUMENTS

| | | | | |
|---|---|---|---|---|
| 3,347,429 A | * | 10/1967 | Ruth, Jr. | A45F 3/04 224/641 |
| 5,040,524 A | * | 8/1991 | Votel | A61F 5/028 2/310 |
| 9,333,108 B2 | * | 5/2016 | Liu | A61F 5/026 |
| 2003/0208146 A1 | * | 11/2003 | Kania | A61F 5/0118 602/19 |
| 2008/0195010 A1 | * | 8/2008 | Lai | A63B 23/0244 602/5 |
| 2011/0152737 A1 | * | 6/2011 | Burke | A61F 5/026 602/19 |
| 2013/0255696 A1 | * | 10/2013 | Fraser | A61H 39/04 128/845 |
| 2014/0074003 A1 | * | 3/2014 | Monden | A61F 5/026 602/19 |
| 2014/0336555 A1 | * | 11/2014 | Barbosa | A61F 5/026 602/19 |

(Continued)

FOREIGN PATENT DOCUMENTS

| CN | 203073021 U | * | 7/2013 |
|---|---|---|---|
| CN | 109620497 A | * | 4/2019 |

(Continued)

*Primary Examiner* — Ophelia A Hawthorne
*Assistant Examiner* — Michael Milo

(57) ABSTRACT

A posture correction brace is disclosed. The brace includes a first member for supporting the back portion of the user, a pair of second members, a third member and a fourth elastic member. The pair of second members extend from the superior side of the first member and extend over the shoulders of the user. The third member extends laterally from the inferior side of the first member and surround the waist portion of the user. The fourth elastic member is connected between the pair of second members at the anterior side in a horizontal direction or between the pair of second members and the third member at the anterior side of the user in a vertical direction. The fourth elastic member is configured to offer resistance to at least one of staying erect or stretching the chest for keeping the shoulder broad.

12 Claims, 16 Drawing Sheets

(56) References Cited

U.S. PATENT DOCUMENTS

2018/0339812 A1* 11/2018 Lee .......................... A45F 3/02
2019/0125397 A1* 5/2019 Arnold .................. A61B 46/10

FOREIGN PATENT DOCUMENTS

DE     102012013386 A1 * 1/2014 ............... A41C 1/10
WO     WO-9965351 A1 * 12/1999 ............. A41F 19/00

* cited by examiner

POSTURE CORRECTION BRACE

FIELD OF INVENTION

The subject matter in general relates to the field of orthotic devices. More particularly, but not exclusively, the subject matter relates to a brace used to correct the posture of a user and thereby train the user to maintain an optimal posture.

BACKGROUND

A good posture can be successfully acquired only when the entire mechanism of the body is under perfect control—Joseph Pilates. The advancements in technology have made a huge portion of the human population to achieve great heights through computers and other computer-based gadgets. Most of the people around the world either sit or stand for long hours in incorrect postures to complete their daily chores using computers which may be detrimental on a long term. For example, many people sitting for long hours at their office desk tend to strain their back muscles and hence tend to unknowingly change their sitting posture by twisting or bending their back bones and muscles that affect their body mechanism in the long run. As another example, people working on electronic assembly or jewelers having to lean over for long hours or a car mechanic having to lean into the car, or kids leaning over their smart device for a long time, eventually affects their entire body structure. In today's world, people need to make an extra effort to exercise or walk to maintain the body mechanism in good condition, failing which might lead to other ailments. It is important to maintain correct posture for the health and aesthetic reasons. Current work scenarios and need of long hours at desk or in front of computers has shown rise in number of people having rounded shoulders or a slouch.

To address the above, people have come up with various devices to either support or monitor the posture even while people are conducting their daily chores. For example, conventional back braces engage around the waist and overlaps at the front of the user thereby providing support to back portion in order keep the posture correct. Further, researchers have developed systems for monitoring posture with alerts and analytics, generated by various sensors that have the ability to sense the backrest inclination with respect to the seat.

It is important for the user to maintain the right posture and hence reduce the stress on the neck and backbone caused due to improper posture habits. The habit of getting accustomed to abnormal posture can be a result of sitting for long hours either in front of computers or while travelling long distances regularly and the likes. The posture braces may be used to correct the abnormal posture of the user and also train the user to maintain the right posture while doing his/her daily chores.

However, the current devices are not designed to train and strengthen the muscles supporting the back, thereby having a long-term effect during posture correction. Most of the current back braces only support or pull the shoulders to improve posture but are not designed to train and strengthen the muscles and help develop muscle memory (i.e., in Type-1, muscles). The proposed back brace focuses on correcting and training the posture muscles (i.e., Type-1) for extended time, thereby help in developing the right muscle memory.

In view of the foregoing discussion, there is a need to provide a permanent solution for correcting the posture of the user by providing constant support and training to rectify and maintain the right posture.

SUMMARY

In an embodiment, a brace to correct the posture of a user using a posture correction brace is disclosed. The brace includes a first member for supporting the back portion of the user, a pair of second members, a third member for supporting around the waist region of the user and a fourth elastic member. The pair of second members extend from the superior side of the first member and are configured to extend over the shoulders of the user. The third member is configured to extend laterally from the inferior side of the first member and surround the waist portion of the user. The fourth elastic member is connected between the pair of second members and the third member at the anterior side of the user in a vertical direction. The fourth elastic member is configured to offer resistance to at least one of staying erect or stretching the chest for keeping the shoulder broad. Alternatively, a monitoring device can be integrated to ensure that the fourth elastic member is optimally engaged to provide the mentioned resistance.

BRIEF DESCRIPTION OF DIAGRAMS

Exemplary embodiments of the present invention will be understood and appreciated more fully from the following detailed description, taken in conjunction with the drawings in which.

DETAILED DESCRIPTION OF THE INVENTION

The following detailed description includes references to the accompanying drawings, which form part of the detailed description. The drawings show illustrations in accordance with example embodiments. The numerals in the figure represent like elements throughout the several views, exemplary embodiments of the present disclosure are described. For convenience, only some elements of the same group may be labelled with numerals. The purpose of the drawings is to describe exemplary embodiments and not for production. Therefore, features shown in the figures are chosen for convenience and clarity of presentation only. Further, the figures may be out of scale, as they are intended for conveying the concept to help understand the working. Moreover, the language used in this disclosure has been principally selected for readability and instructional purposes and may not have been selected to delineate or circumscribe the inventive subject matter, resort to the claims being necessary to determine such inventive subject matter. These example embodiments are described in enough details to enable those skilled in the art to practice the present subject matter. However, it will be apparent to one of ordinary skill in the art that the present invention may be practiced without these specific details. The embodiments can be combined, other embodiments can be utilized, or structural and logical changes can be made without departing from the scope of the invention. The following detailed description is, therefore, not to be taken as a limiting sense.

In this document, the terms "a" or "an" are used, as is common in patent documents, to include one or more than one. In this document, the term "or" is used to refer to a non-exclusive "or," such that "a or b" includes "a but not b," "b but not a," and "a and b," unless otherwise indicated.

Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Figure 1:
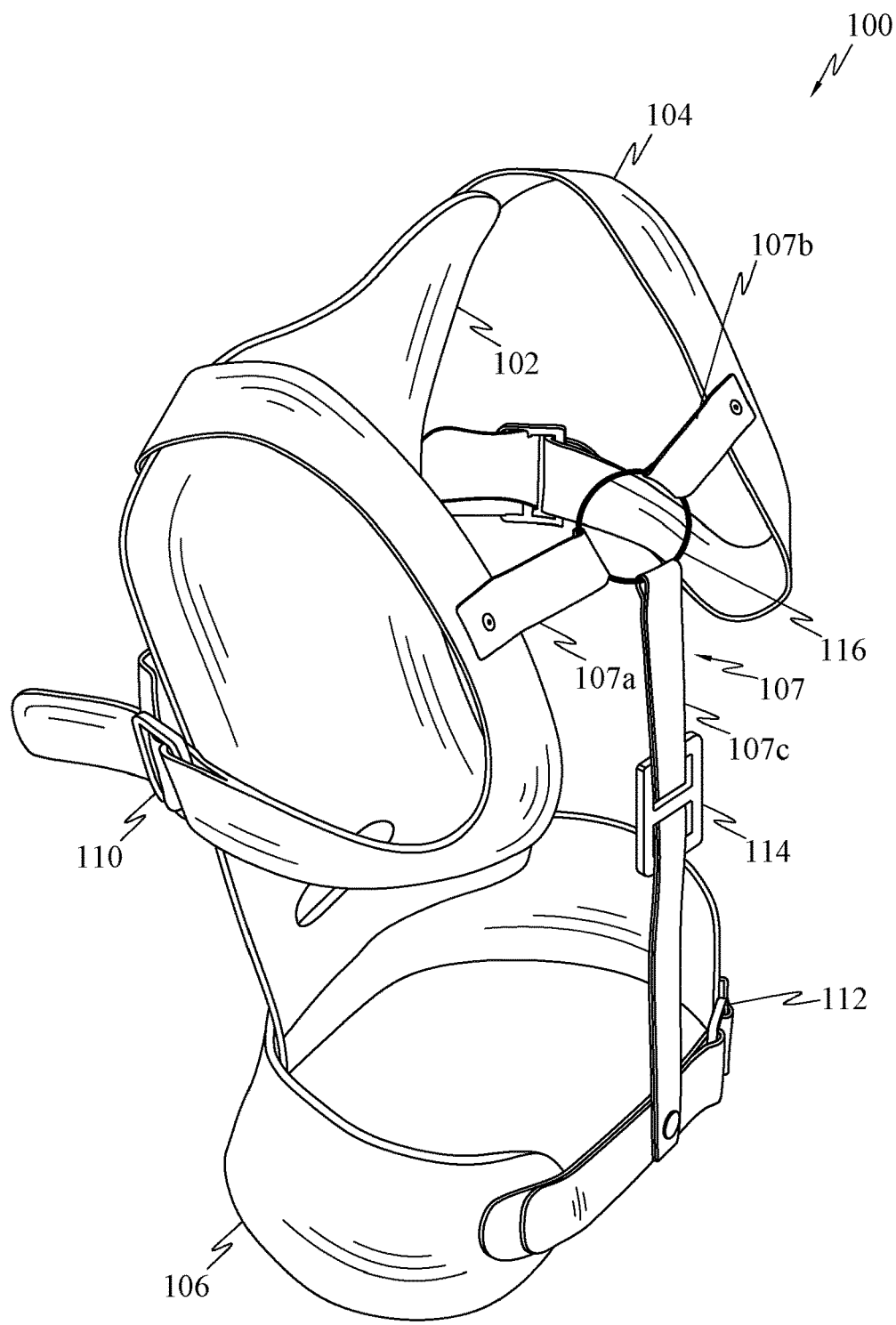
FIG. 1 illustrates a posture correction brace 100, in accordance with an embodiment.

FIG. 1 illustrates a posture correction brace 100, in accordance with an embodiment. The brace 100 may comprise a first member 102. The first member 102 may be configured to cover the back portion of a user. The first member 102 may be made using a first material. The first material may be almost non-stretchable.

Referring to FIG. 1, the brace 100 may comprise a pair of second members 104 along with a pair of first tension adjusting device 110. The pair of second members 104 may extend from the superior side of the first member 102. The pair of second members 104 may be either permanently fixed to the first member 102 or detachably attached to the first member 102. Each of the pair of second members 104 may be configured to extend over the right and left shoulders of the user, respectively. Further, each of the pair of second member 104 may be made using a second material. The second material may be a nylon strap, or any other semi-elastic strap based on requirements.

In one embodiment, the second member 104 may be more stretchable than the first member 102.

In one embodiment, the strap may be in the form of a string, elastic band, tension spring or any other fabric with enough stretchability to create the required tension to provide the functionally required resistance.

Each of the pair of first tension adjusting devices 110 in FIG. 1, may be coupled to each second member 104. Further, each of the pair of first tension adjusting devices 110 may be configured to adjust the tension of each of the pair of second members 104. The pair of first tension adjusting devices 110 may be any kind of buckles that may include cam buckles, ratchet buckles, roller buckles, side release buckles, slide buckles or snap buckles.

Referring to FIG. 1 the brace 100 may comprise a third member 106. The third member 106 may extend laterally from the inferior side of the first member 102. Further, the third member 106 may be configured to surround a portion of the waist of the user. A portion of the third member 106 on the back region of the user may be either fixed to the first member 102 or may be detachably attached to the first member 102.

In one embodiment, the third member 106 may be made using a third material. The third member 106 may be more stretchable than the first member 102. The third member 106 may be less than or almost as stretchable as the second member 104. The third member 106 may be an adjustable belt or a Velcro belt.

The brace 100 may comprise a second tension adjusting device 112. The second tension adjusting device 112 may be coupled to the third member 106. The second tension adjusting device 112 may be any kind of buckle that may include cam buckles, ratchet buckles, roller buckles, side release buckles, slide buckles or snap buckles. The third member 106 may be configured to adjust and fit to the waist size of the user at the waist region by adjusting the second tension adjusting device 112.

Referring to FIG. 1, the brace 100 may comprise a fourth elastic member 107. The fourth elastic member 107 may be connected between the pair of second members 104 and the third member 106 at the anterior side of the user in the vertical direction. The fourth elastic member 107 may be made of a fourth material.

Just to differentiate the fourth member 107 by its functionality, the fourth member may be referred along with the usage of the word "elastic" in the document. E.g., "fourth elastic member" or "fourth elastic component".

In one embodiment, the fourth material may be in the form of any material or fabric that may be capable of providing the required stretch resulting into a tension that may provide the required resistance. The fourth material may be a rubber, a stretchable rope/string, an elastic band or a tension spring based on the design.

In one embodiment, the fourth elastic member 107 may be more stretchable than the first member 102, second member 104 and the third member 106. The fourth elastic member 107 may be configured to offer resistance to at least one of either sitting erect or stretching the chest wide.

In one embodiment, the first material may be relatively non-stretchable or hard. The second material may be non-stretchable or semi-stretchable to provide flexibility around the shoulders. The third material may be same as the second material, with almost the same stretchability. The purpose of using the third member may be to fasten the brace around the waist. The fourth material may be more stretchable by material or by design than the first, second and third materials. The fourth material may provide enough tension to produce the required resistance in comparison to the second, third and the fourth materials.

As an example, the fourth elastic member 107 may be made using the fourth material (example: Rubber) that may be more stretchable than the second material (example: Nylon), of the second member 104.

Referring to FIG. 1, the fourth elastic member 107 may be coupled to a third tension adjusting device 114. The third tension adjusting device 114 may be any kind of buckles that may include cam buckles, ratchet buckles, roller buckles, side release buckles, slide buckles or snap buckles. The third tension adjusting device 114 may be configured to alter the resistance offered by the fourth elastic member 107 to at least one of either sitting erect or stretching the chest wide/broad of the user, based on the user requirement.

In an embodiment, as illustrated in FIG. 1, the fourth elastic member 107 may comprise a first connector 116, a first strap 107a, second strap 107b and a third strap 107c. The first end of the first strap 107a may be connected to any one of the pair of second members 104. The first end of the second strap 107b may be connected to the other second member 104. The second ends of the first strap 107a and the second strap 107b may be connected to the first connector 116. The first end of the third strap 107c may be connected to the third member 106 and the second end of the third strap 107c may be connected to the first connector 116. The third strap 107c may include the third tension adjusting device 114. The third tension adjusting device 114 may be used to pull the third strap 107c in the vertical direction along a single line for optimizing the resistance offered by the fourth elastic member 107.

Alternatively, in one embodiment, the fourth elastic member 107 may comprise a first connector 116, a first strap 107a and a second strap 107b. The first end of the first strap 107a may be connected to any one of the pair of second members 104. The first end of the second strap 107b may be connected to the other second member 104. The second ends of the first strap 107a and the second strap 107b may be connected to the first connector 116. The first strap 107a and the second strap 107b may be configured to provide resistance in the horizontal direction for optimizing the resistance offered by the fourth elastic member 107.

Figure 2:
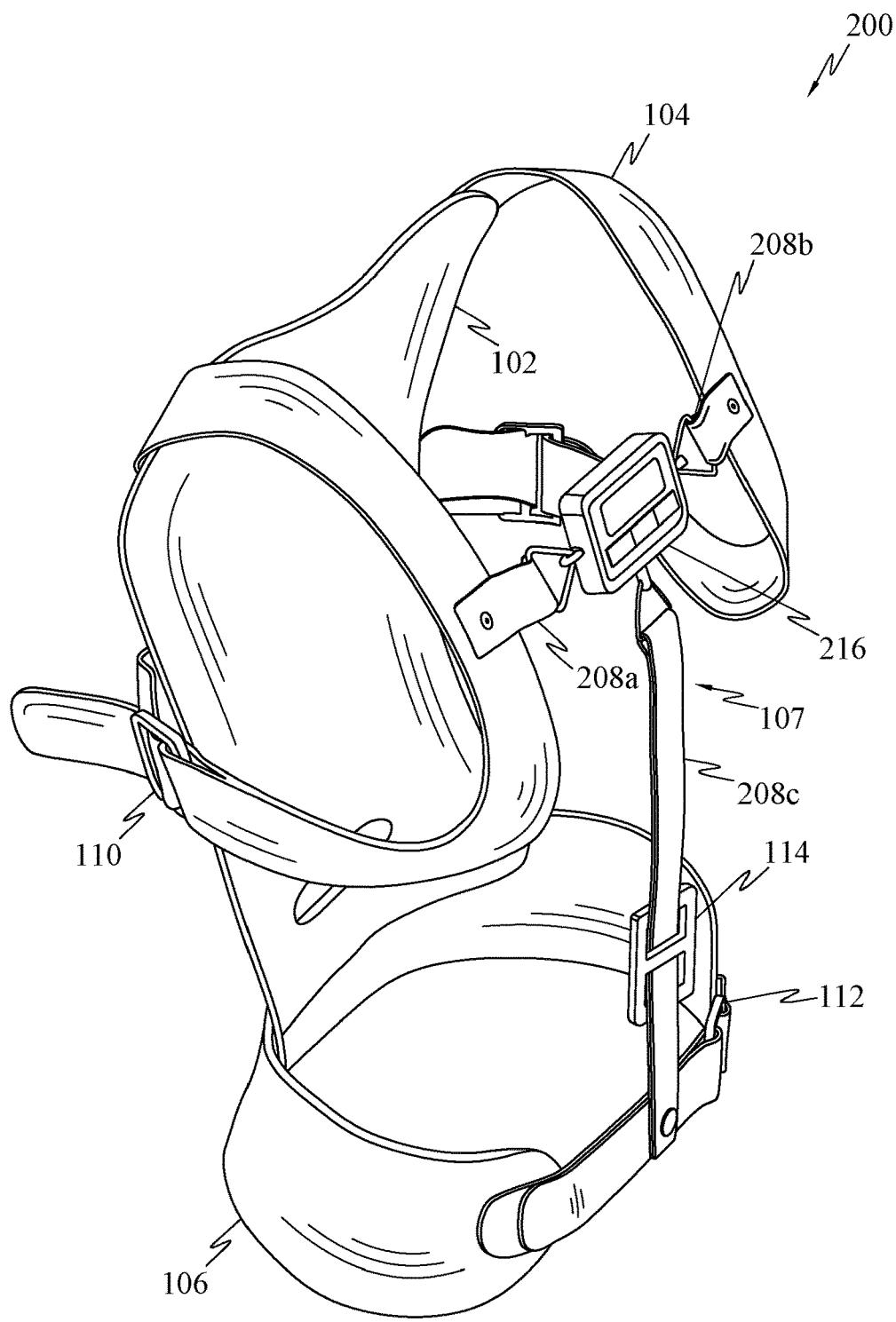
FIG. 2 illustrates a posture correction brace 200, in accordance with an embodiment.

FIG. 2 illustrates a posture correction brace 200, in accordance with an embodiment. The brace 200 may include a tension monitoring device 216. The tension monitoring device 216 may comprise swivels for connecting the straps. The tension monitoring device 216 may comprise an electronic unit and a tension sensor. The tension sensor may be configured to sense the tension in the fourth elastic member 107. The electronic unit may be configured to monitor the tension sensor, display the tension in the fourth elastic member 107 and may trigger an alarm when the tension in the fourth elastic member 107 deviates from a predetermined value of tension.

The fourth elastic member 107 may comprise a fourth strap 208a, a fifth strap 208b and a sixth strap 208c. The first end of the fourth strap 208a may be connected to any one of the pair of second members 104. The first end of the fifth strap 208b may be connected to the other second member 104. The second ends of the fourth strap 208a and the fifth strap 208b may be connected to the tension monitoring device 216 at the left swivel and the right swivel respectively. The first end of the sixth strap 208c may be connected to the third member 106 and the second end of the sixth strap 208c may be connected to the tension monitoring device 216 using the lower swivel. The sixth strap 208c may include the third tension adjusting device 114. The third tension adjusting device 114 may be used to pull the sixth strap 208c in the vertical direction along a single line for optimizing the resistance offered by the fourth elastic member 107. The fourth strap 208a, the fifth strap 208b and the sixth strap 208c of the fourth elastic member 107 may be configured to anchor around the tension monitoring device 216 while providing the optimal resistance. The tension monitoring device 216 may be configured monitor the tension in the fourth elastic member 107 and can alert the user in case of change in predetermined tension range.

Alternatively, in one embodiment, the fourth elastic member 107 may comprise a fourth strap 208a and a fifth strap 208b. The first end of the fourth strap 208a may be connected to any one of the pair of second members 104. The first end of the fifth strap 208b may be connected to the other second member 104. The second ends of the fourth strap 208a and the fifth strap 208b may be connected to the tension monitoring device 216 at the left swivel and the right swivel respectively. The fourth strap 208a and the fifth strap 208b may be configured to anchor on either side of the tension monitoring device 216 in the horizontal direction for optimizing the resistance offered by the fourth elastic member 107. The tension monitoring device 216 may be configured monitor the tension in the fourth elastic member 107.

Figure 3A:
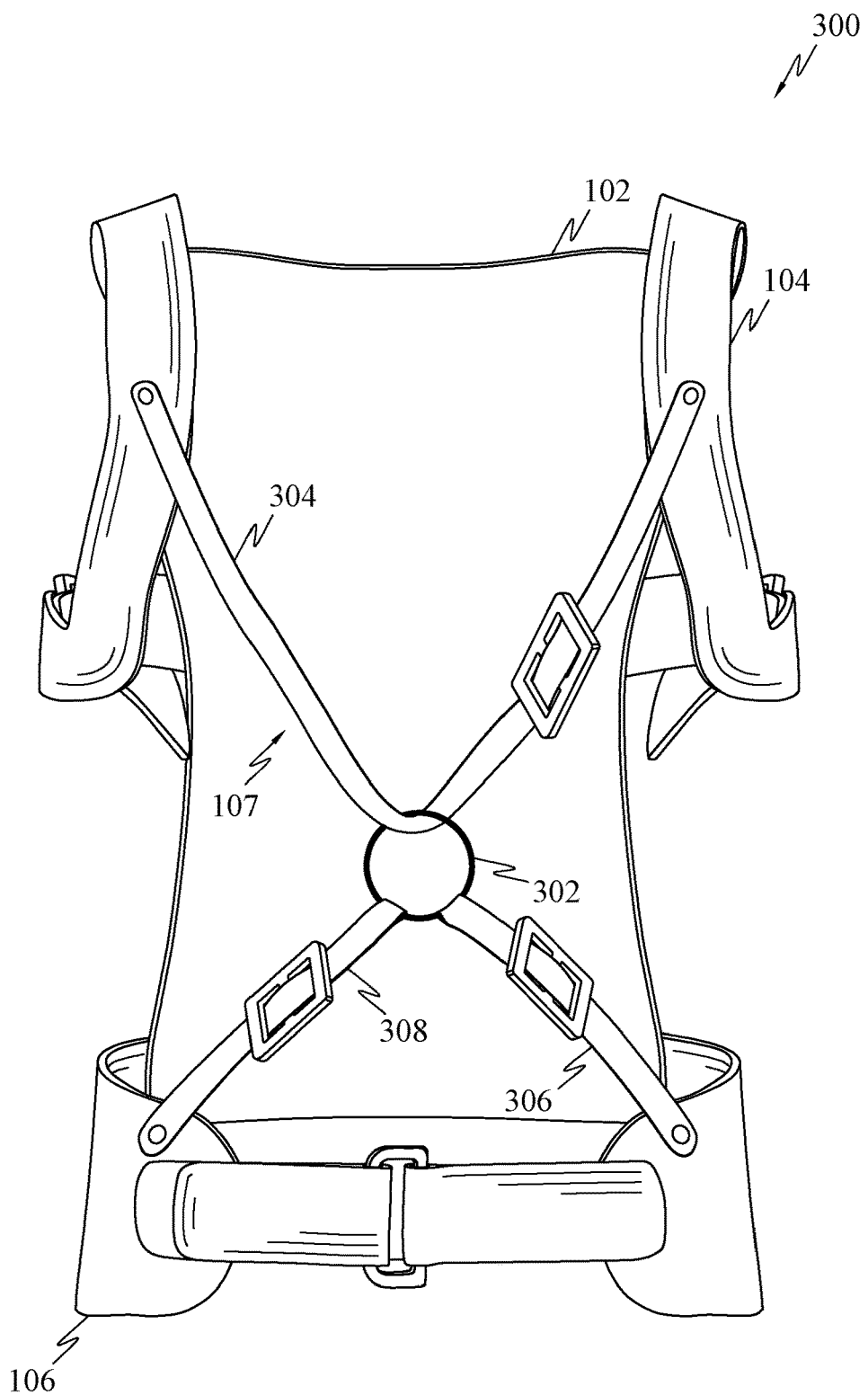
FIG. 3A illustrates the posture correction brace 300, in accordance with another embodiment.

FIG. 3A illustrates a posture correction brace 300, in accordance with an embodiment. The fourth elastic member 107 of the brace 100 may comprise a second connector 302, a seventh strap 304, an eighth strap 306 and a ninth strap 308. The first end of the seventh strap 304 may be connected to one of the pair of second members 104. The second end of the seventh strap 304 may be connected to the other second member 104 via the second connector 302. The first end of the eighth strap 306 and the first end of the ninth strap 308 may both be connected to the second connector 302. Further, the second end of the eighth strap 306 may be connected to one side of the third member 106. The second end of the ninth strap 308 may be connected to the other side of the third member 106.

Figure 3B:
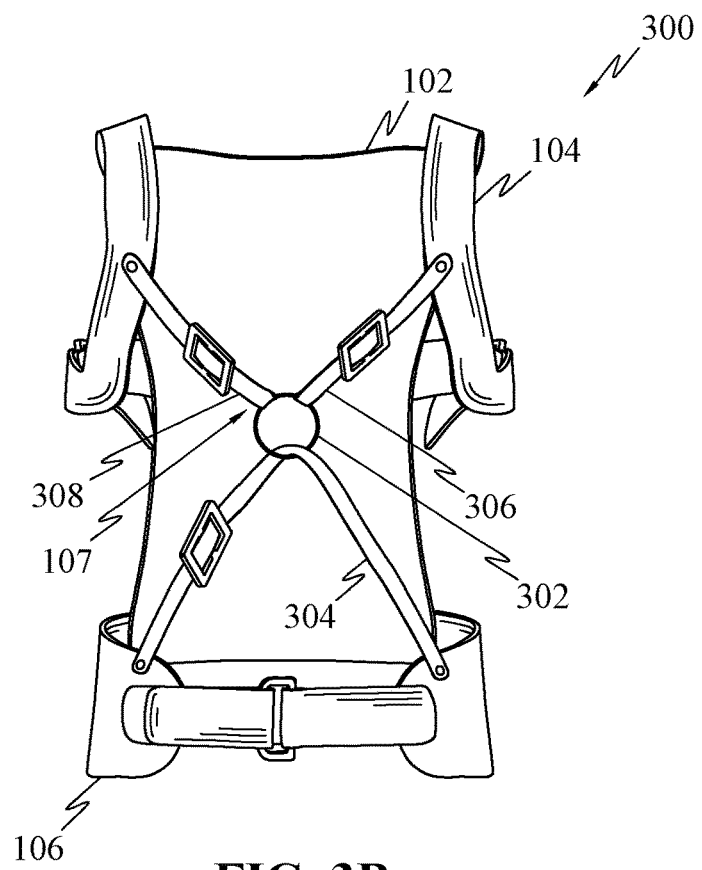
FIG. 3B illustrates the posture correction brace 300, in accordance with another embodiment.

FIG. 3B illustrates the posture correction brace 300, in accordance with another embodiment. Accordingly, the first end of the eighth strap 306 and the first end of the ninth strap 308 may both be connected to the second connector 302. Further, the second end of the eighth strap 306 may be connected to one of the pair of second members 104. The second end of the ninth strap 308 may be connected to the other second member 104. The first end of the seventh strap 304 may be connected to one side of the third member 106. The second end of the seventh strap 304 may be connected to the other side of the third member 106 via the second connector 302.

Figure 3C:
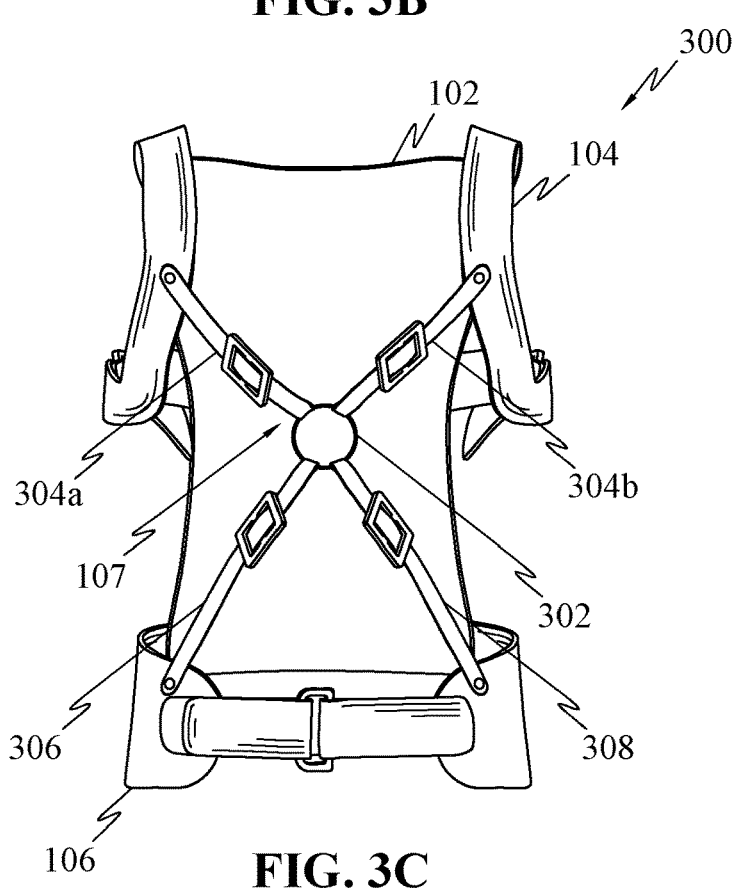
FIG. 3C illustrates the posture correction brace 300, in accordance with another embodiment.

FIG. 3C illustrates the posture correction brace 300, in accordance with another embodiment. Accordingly, the seventh strap 304 may comprise two parts 304a and 304b. The first ends of each part of the seventh strap 304a and 304b may be connected to each of the pair od second members 104. The second ends of each part of the seventh strap 304a and 304b may be connected to the second connector 302. The first end of the eighth strap 306 and the first end of the ninth strap 308 may both be connected to the second connector 302. Further, the second end of the eighth strap 306 may be connected to one side of the third member 106. The second end of the ninth strap 308 may be connected to the other side of the third member 106.

Figure 3D:
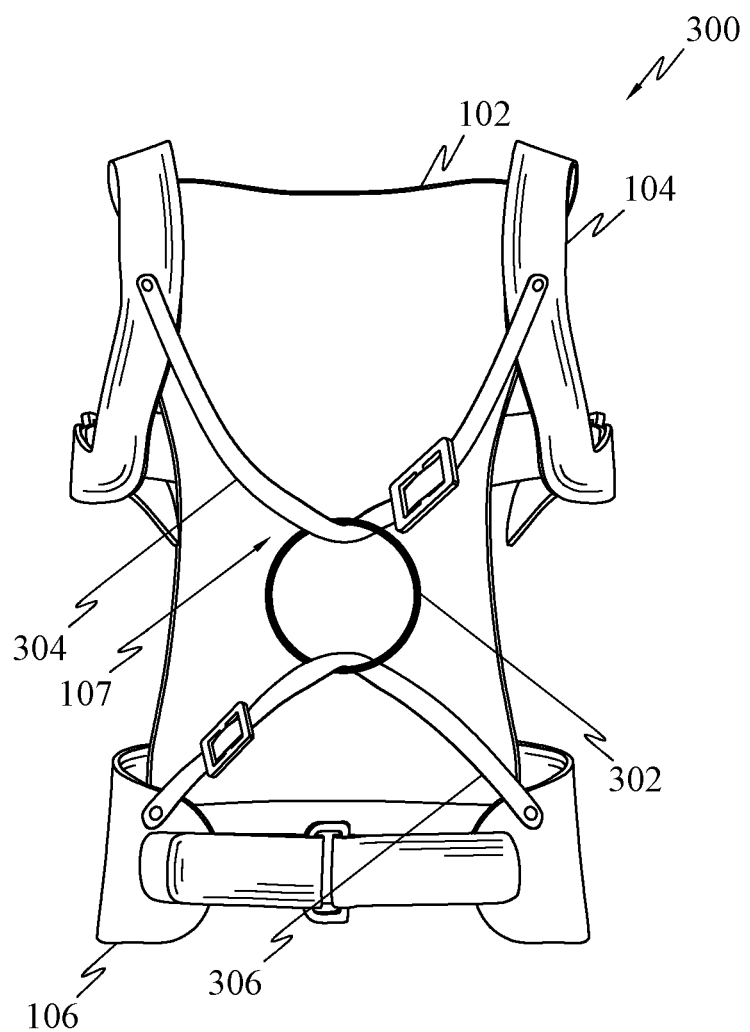
FIG. 3D illustrates the posture correction brace 300, in accordance with another embodiment.

FIG. 3D illustrates the posture correction brace 300, in accordance with another embodiment. Accordingly, the first end of the seventh strap 304 may be connected to one of the pair of second members 104. The second end of the seventh strap 304 may be connected to the other second member 104 via the second connector 302. The first end of the eighth strap 306 may be connected to one side of the third member 106. The second end of the eighth strap 306 may be connected to the other side of the third member 106 via the second connector 302.

In one embodiment, the seventh strap 304, the eighth strap 306 and the ninth strap 308 may include a third tension adjusting device each 114. The third tension adjusting device 114 on each of the eighth strap 306 and the ninth strap 308 may be used to provide a primary resistance in a horizontal direction across the chest and in an oblique direction across the chest of user. The resistance in the horizontal direction across the chest may help in correcting the hollowing of shoulders by training and strengthening the shoulder and other supporting back muscles. The resistance in the oblique direction may train and strengthen the supporting muscles that help keep the spine straight and erect and thereby developing muscle memory to maintain an optimal posture as required by the user.

FIG. 4A, FIG. 4B, FIG. 4C and FIG. 4D illustrate a posture correction brace 400, in accordance with an embodiment. The brace 400 may include a tension monitoring device 410. The tension monitoring device 410 may comprise swivels for connecting the straps. The tension monitoring device 410 may comprise an electronic unit and a tension sensor. The tension sensor may be configured to sense the tension in the fourth elastic member 107. The electronic unit may be configured to monitor the tension sensor, display the tension in the fourth elastic member 107 and may trigger an alarm when the tension in the fourth elastic member 107 deviates from a predetermined value of tension.

Figure 4A:
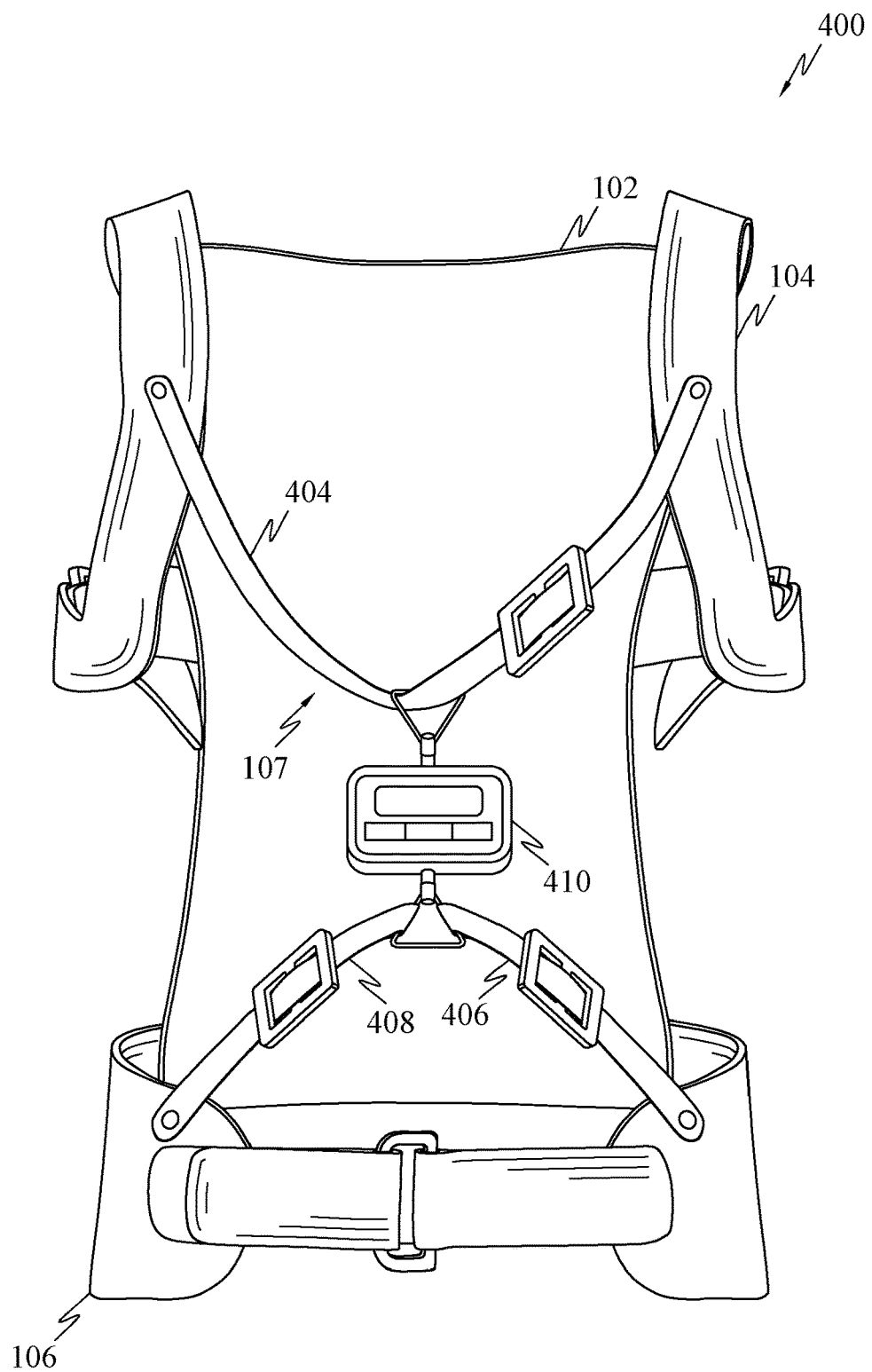
FIG. 4A illustrates the posture correction brace 400, in accordance with an embodiment.

FIG. 4A illustrates the posture correction brace 400, in accordance with an embodiment. Accordingly, the fourth elastic member 107 of the brace 400 may comprise a tenth strap 404, an eleventh strap 406 and a twelfth strap 408. The tenth strap 404 may have first end connected to one of the pair of second members 104. The second end of the tenth strap 404 may be connected to the other second member 104 via the upper swivel of the tension monitoring device 410. The first end of the eleventh strap 406 and the first end the twelfth strap 408 may be connected to the bottom swivel of the tension monitoring device 410. The second ends of the eleventh strap 406 and the twelfth strap 408 may be connected to either side of the third member 106. The eleventh strap 406 and the twelfth strap 408 may include a third tension adjusting device 114 each.

Figure 4B:
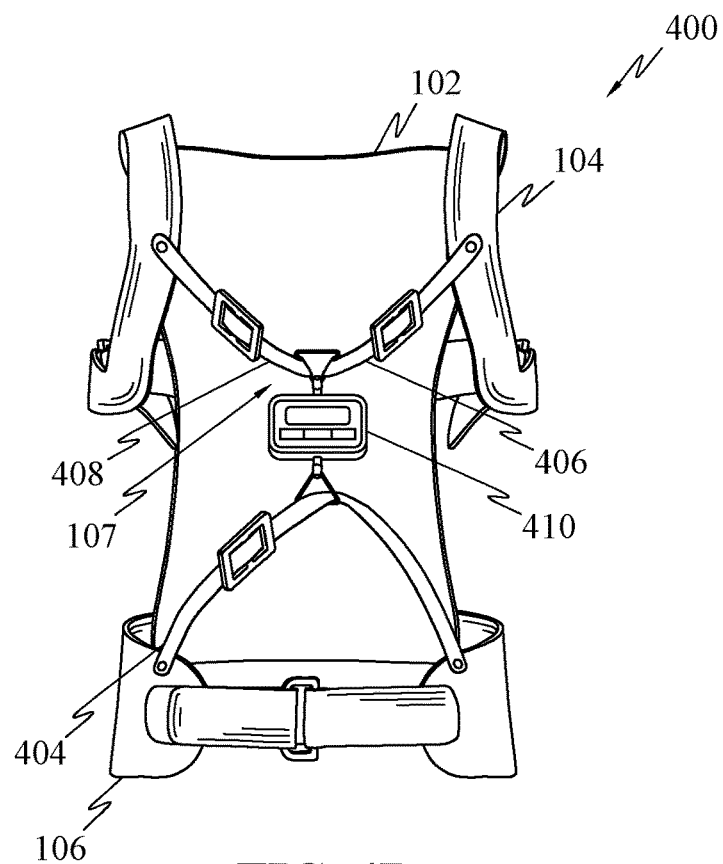
FIG. 4B illustrates the posture correction brace 400, in accordance with an embodiment.

FIG. 4B illustrates the posture correction brace 400, in accordance with an embodiment. Accordingly, the first end of the eleventh strap 406 and the first end the twelfth strap 408 may be connected to upper swivel of the tension monitoring device 410. The second end of the eleventh strap 406 may be connected to one of the pair of second members 104. Further, the second end of the twelfth strap 408 may be connected to the other second member 104. The tenth strap 404 may have first end connected to one side of the third member 106. The second end of the tenth strap 404 may be connected to the other side of the third member 106 via the bottom swivel of the tension monitoring device 410.

Figure 4C:
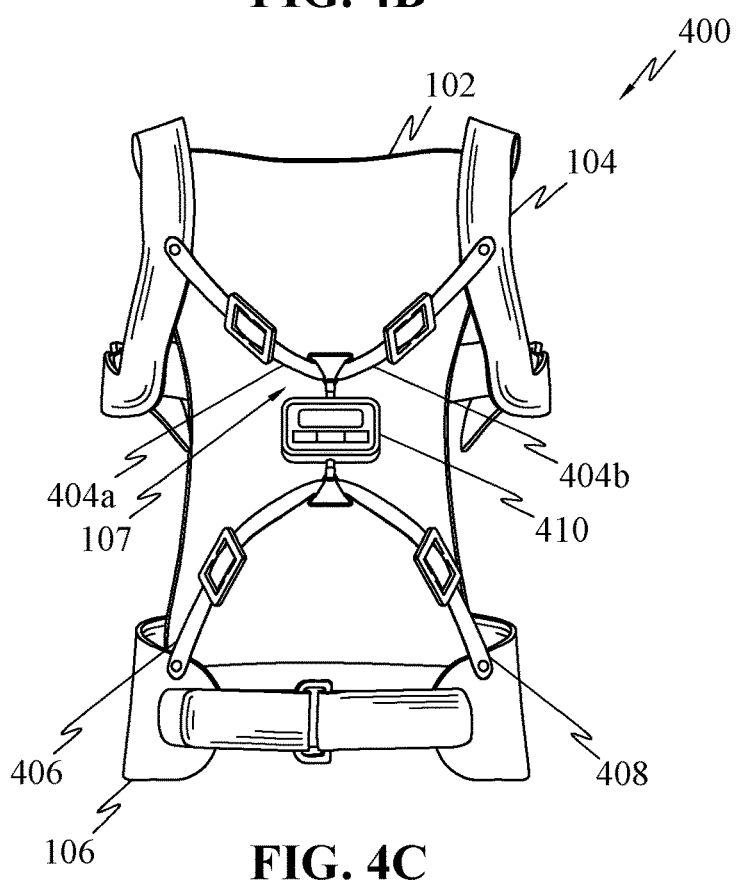
FIG. 4C illustrates the posture correction brace 400, in accordance with an embodiment.

FIG. 4C illustrates the posture correction brace 400, in accordance with an embodiment. Accordingly, the tenth strap 404 may comprise two parts 404a and 404b. The first ends of each part of the tenth strap 404a and 404b may be connected to each of the pair od second members 104. The second ends of each part of the tenth strap 404a and 404b may be connected to the to upper swivel of the tension monitoring device 410. The first end of the eleventh strap 406 and the first end of the twelfth strap 408 may both be connected to the to lower swivel of the tension monitoring device 410. Further, the second end of the eleventh strap 406 may be connected to one side of the third member 106. The second end of the twelfth strap 408 may be connected to the other side of the third member 106.

Figure 4D:
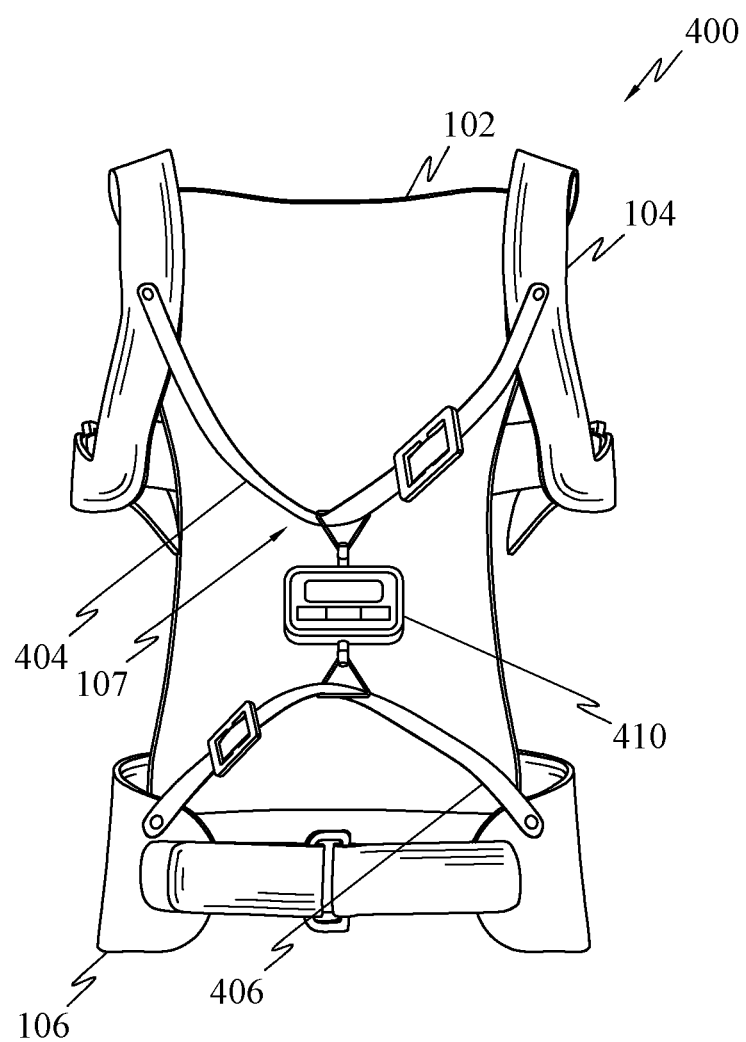
FIG. 4D illustrates the posture correction brace 400, in accordance with an embodiment.

FIG. 4D illustrates the posture correction brace 400, in accordance with an embodiment. Accordingly, the first end of the tenth strap 404 may be connected to one of the pair of second members 104. The second end of the tenth strap 404 may be connected to the other second member 104 via the upper swivel of the tension monitoring device 410. The first end of the eleventh strap 406 may be connected to one side of the third member 106. The second end of the eleventh strap 406 may be connected to the other side of the third member 106 via to lower swivel of the tension monitoring device 410.

The third tension adjusting device 114 on each of the tenth strap 404, eleventh strap 406 and the twelfth strap 408 may be used to provide a resistance in a horizontal direction across the chest and in an oblique direction on the sides of the torso of user. The resistance in the horizontal direction across the chest may help in correcting the hollowing of shoulders by strengthening the shoulder muscles. The resistance in the oblique direction may strengthen the torso and spine supporting muscles used in sitting erect as well as with wide chest and may thereby help in providing stability to the body while maintaining the right posture. The tenth strap 404, eleventh strap 406 and the twelfth strap 408 of the fourth elastic member 107 may be configured to anchor around the tension monitoring device 410 while providing the optimal predetermined resistance. The tension monitoring device 410 may be configured monitor the tension in the fourth elastic member 107.

Figure 5:
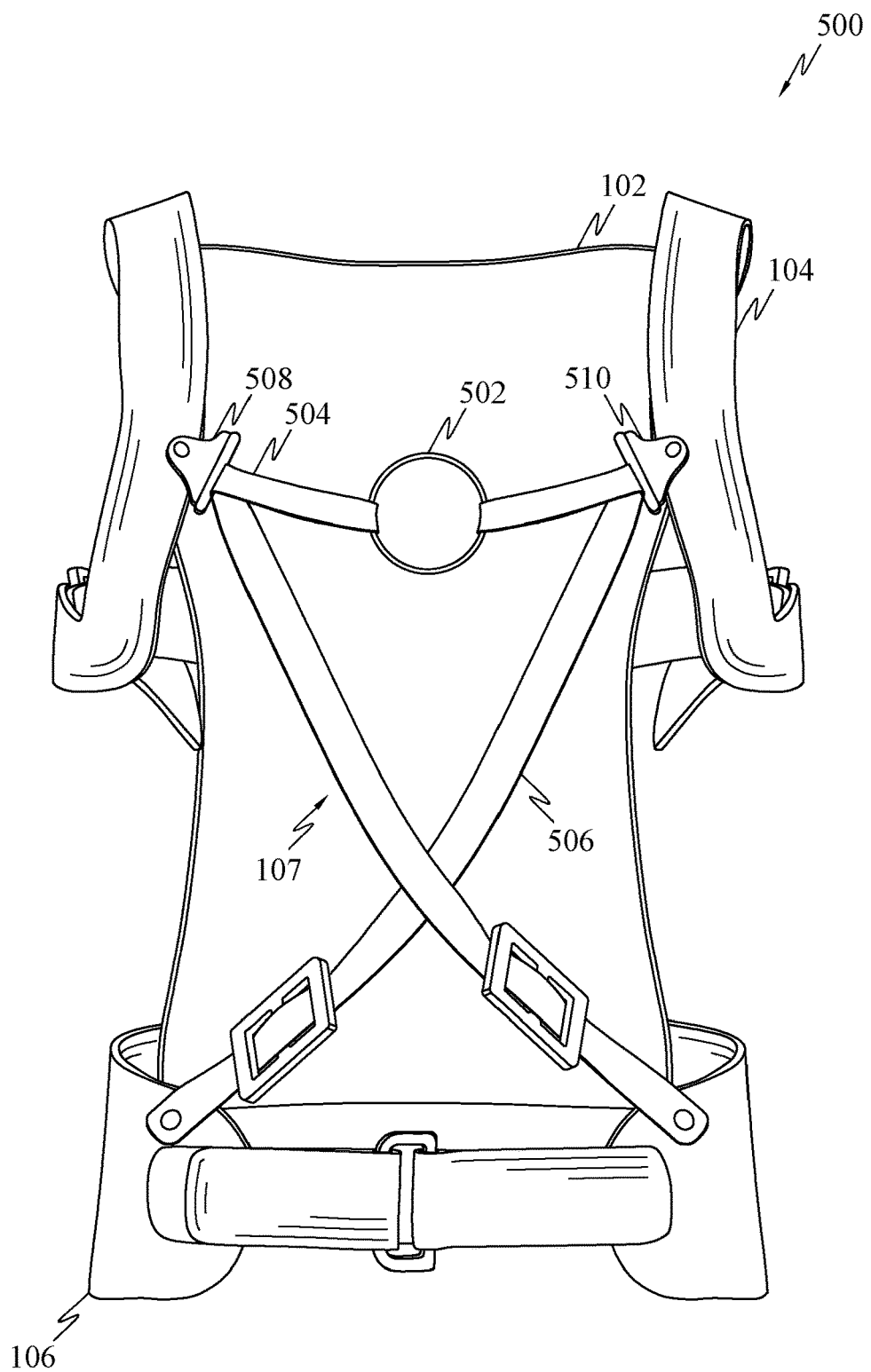
FIG. 5 illustrates a posture correction brace 500, in accordance with an embodiment.

FIG. 5 illustrates a posture correction brace 500, in accordance with an embodiment. The fourth elastic member 107 of the brace 500 may comprise a third connector 502, a first swivel 508 coupled to one of the pair of second members 104, a second swivel 510 coupled to the other second member 104, a thirteenth strap 504 and a fourteenth strap 506. The first end of the thirteenth strap 504 may be connected to the third connector 502. The second end of the thirteenth strap 504 may be connected to one side of the third member 106 via the first swivel 508, wherein the side of the third member 106 coupled to the second end of the thirteenth strap 504 may be located diagonally opposite to the first swivel 508. The first end of the fourteenth strap 506 may be connected to the third connector 502. The second end of the fourteenth strap 506 may be connected to the other side of the third member 106 via the second swivel 510, wherein the other side of the third member 106 coupled to the second end of the fourteenth strap 506 may be diagonally opposite to the second swivel 510. The thirteenth strap 504 and the fourteenth strap 506 may include a third tension adjusting device 114 each. The third tension device 114 on each of the thirteenth strap 504 and the fourteenth strap 506 may be configured to provide an enhanced diagonal resistance, spanning across the chest of the user from the shoulder till the waist of the user. The enhanced diagonal resistance may be useful for users who may slouch and whose shoulders may hollow inwards.

Figure 6:
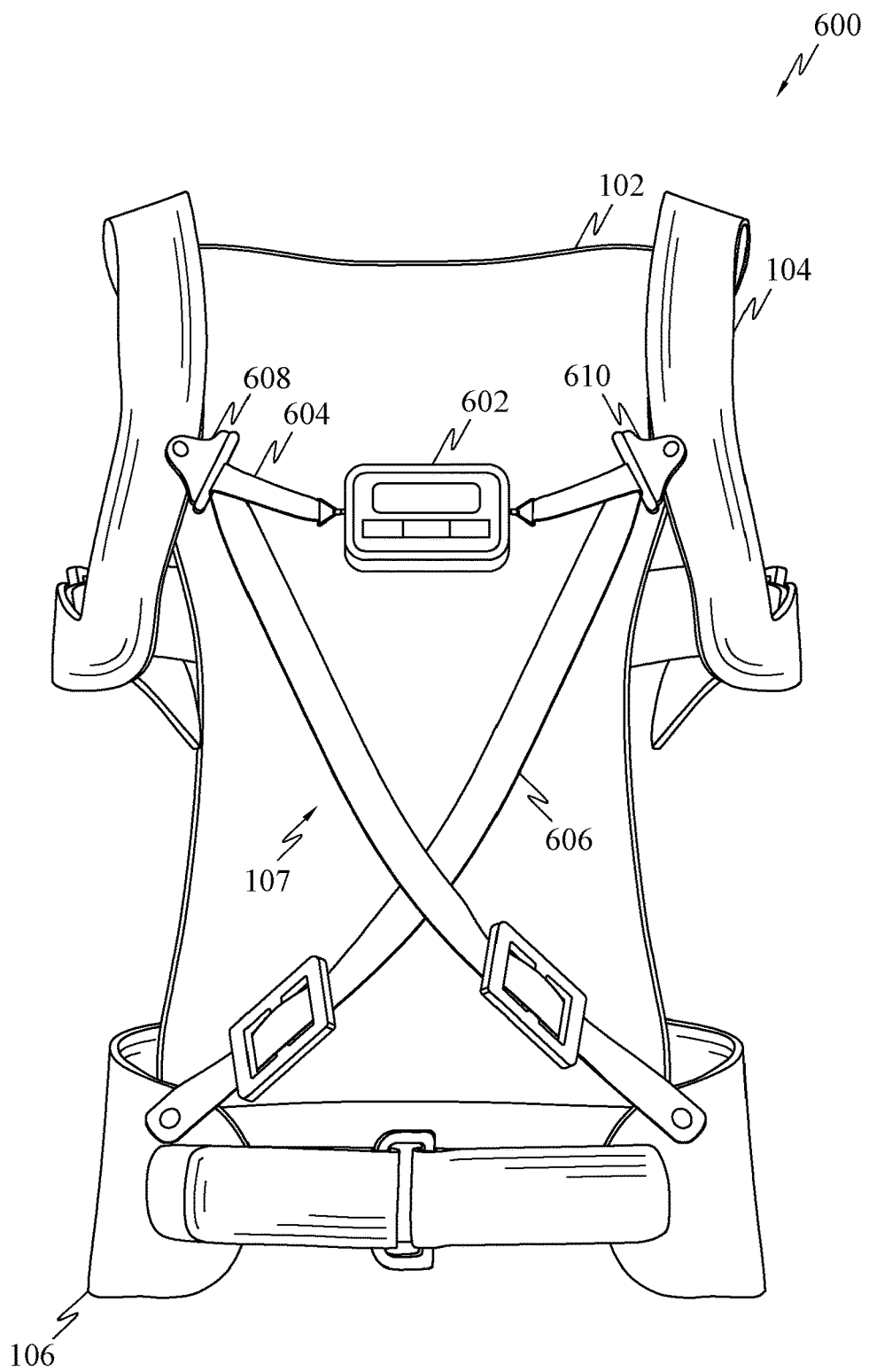
FIG. 6 illustrates a posture correction brace 600, in accordance with an embodiment.

FIG. 6 illustrates a posture correction brace 600, in accordance with an embodiment. The brace 600 may include a tension monitoring device 602. The tension monitoring device 602 may comprise swivels for connecting the straps. The tension monitoring device 602 may comprise an electronic unit and a tension sensor. The tension sensor may be configured to sense the tension in the fourth elastic member 107. The electronic unit may be configured to monitor the tension sensor, display the tension in the fourth elastic member 107 and may trigger an alarm when the tension in the fourth elastic member 107 deviates from a predetermined value of tension. The tension monitoring device 602 may have an added advantage that instead of manually monitoring that one stays in predefined posture, the monitoring device may be integrated in the brace, that may help in notifying the user when they slouch or round their shoulder or hollow their chest.

The fourth elastic member 107 of the brace 600 may comprise, a third swivel 608 coupled to one of the pair of second member 104, a fourth swivel 610 coupled to the other second member 104, a fifteenth strap 604 and a sixteenth strap 606. The first end of the fifteenth strap 604 may be connected to the left swivel of the tension monitoring device 602. The second end of the fifteenth strap 604 may be connected to one side of the third member 106 via the third swivel 608, wherein the side of the third member 106 that may be coupled to the second end of the fifteenth strap 604 may be diagonally opposite to the third swivel 608. The first end of the sixteenth strap 606 may be connected to the right swivel of tension monitoring device 602. The second end of the sixteenth strap 606 may be connected to the other side of the third member 106 via the fourth swivel 610, wherein the other side of the third member 106 that may be coupled to the second end of the sixteenth strap 606 may be diagonally opposite to the fourth swivel 610. The fifteenth strap 604 and the sixteenth strap 606 may include a third tension adjusting device 114 each. The third tension adjusting device on each of the fifteenth strap 604 and the sixteenth strap 606 may be configured to provide an enhanced diagonal resistance, spanning across the chest of the user from the shoulder till the waist of the user. The enhanced diagonal resistance may be useful for users who may slouch and whose shoulders may hollow inwards. The fifteenth strap 604 and the sixteenth strap 606 of the fourth elastic member 107 may be configured to anchor across the tension monitoring device 602 while providing the optimal predetermined resistance. The tension monitoring device 602 may be configured to monitor the tension in the fourth elastic member 107.

Figure 7:
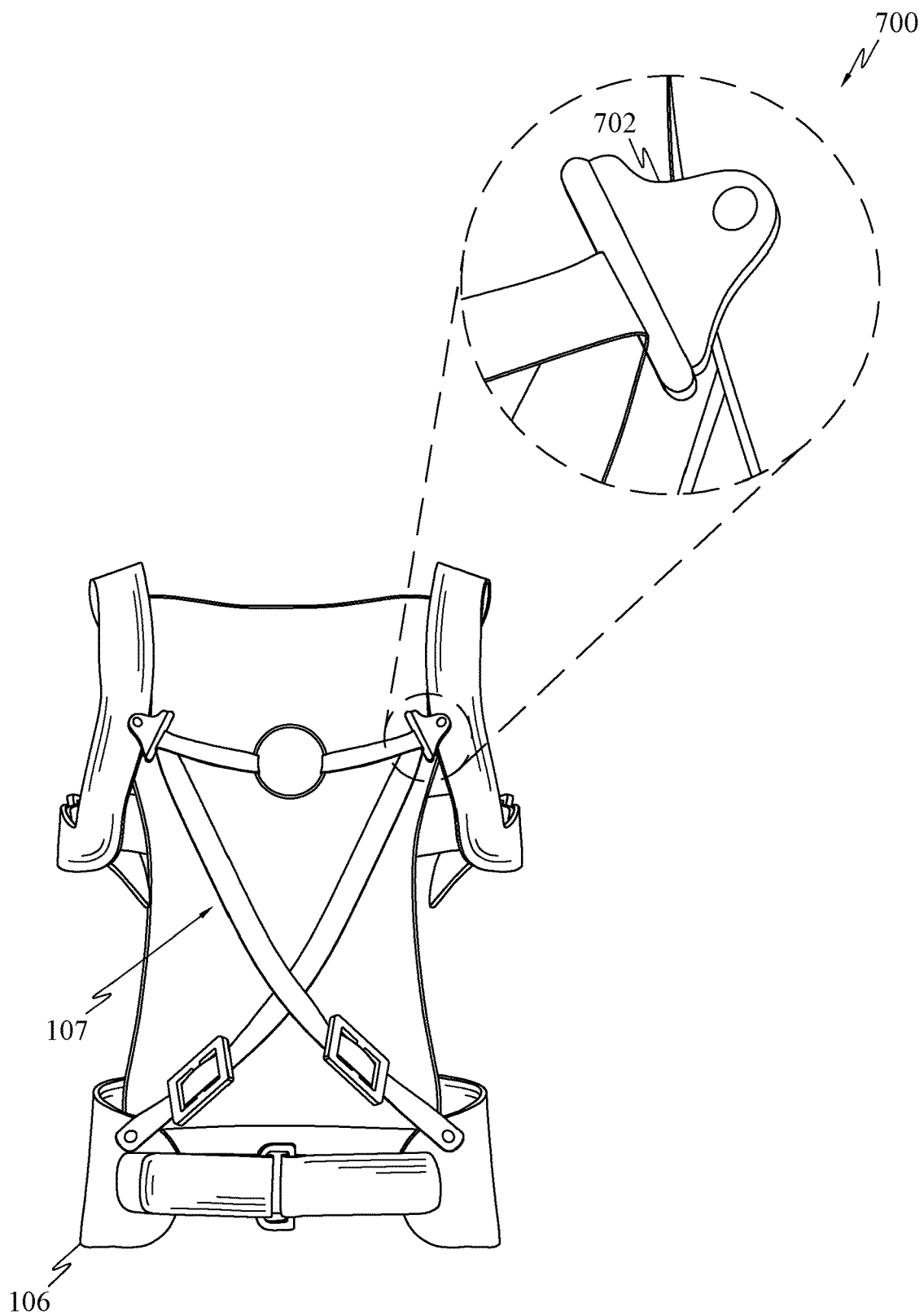
FIG. 7 illustrates is a detailed view of a swivel of a posture correction brace, in accordance with an embodiment.

FIG. 7 illustrates is a detailed view of a swivel of a posture correction brace, in accordance with an embodiment. The combination and specific variation of the straps, tension adjusting devices, swivels, buckles etc. may be used based on design to improve sizing, feasibility and flexibility of the described brace 700. For example, the swivels 702 on the pair of second members 104 at the shoulder as shown in FIG. 7 may be used to achieve the change in direction, where a freely rotating part may be used to automatically optimize the angle and a roller pin mechanism may be used for easy passing of the straps.

Figure 8A:
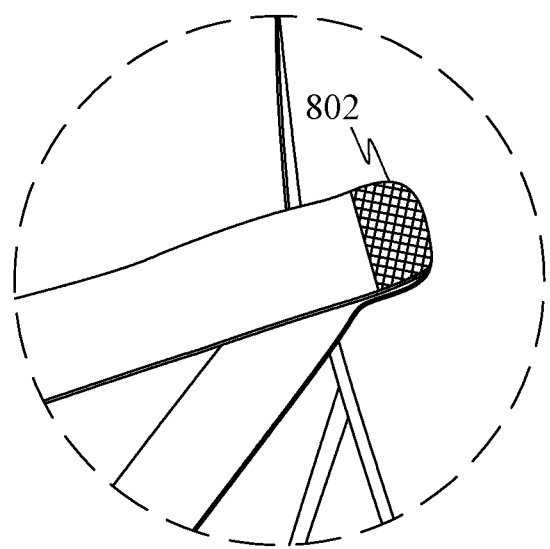
FIG. 8A illustrates a stitch-type connection for connecting the members of the posture correction brace, in accordance with an embodiment.

FIG. 8A illustrates a stitch-type connection for connecting the members of the posture correction brace, in accordance with an embodiment. The connections between the first member 102, pair of second members 104, the third member 106 and the fourth elastic member 107 may be a stitch-type 802 connection. The stitch-type 802 connection may be wherein each member may be stitched onto each other member to establish a connection.

Figure 8B:
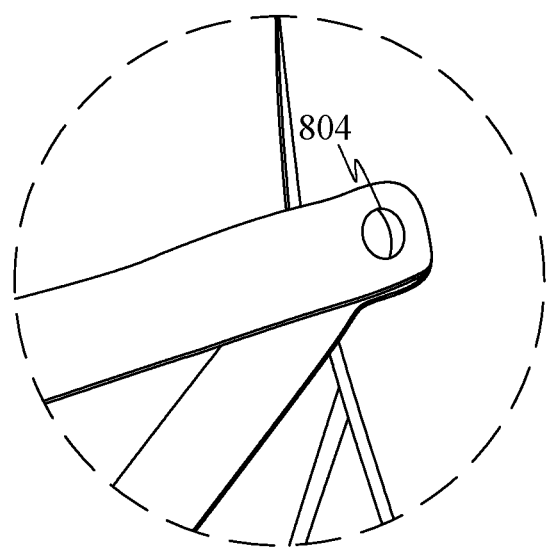
FIG. 8B illustrates a button-type connection for connecting the members of the posture correction brace, in accordance with an embodiment.

FIG. 8B illustrates a button-type connection for connecting the members of the posture correction brace, in accordance with an embodiment. The connections between the first member 102, pair of second members 104, the third member 106 and the fourth elastic member 107 may be a button-type 804 connection. The button-type 804 connection can be wherein each member may be buttoned onto each other member to establish a connection.

Figure 9:
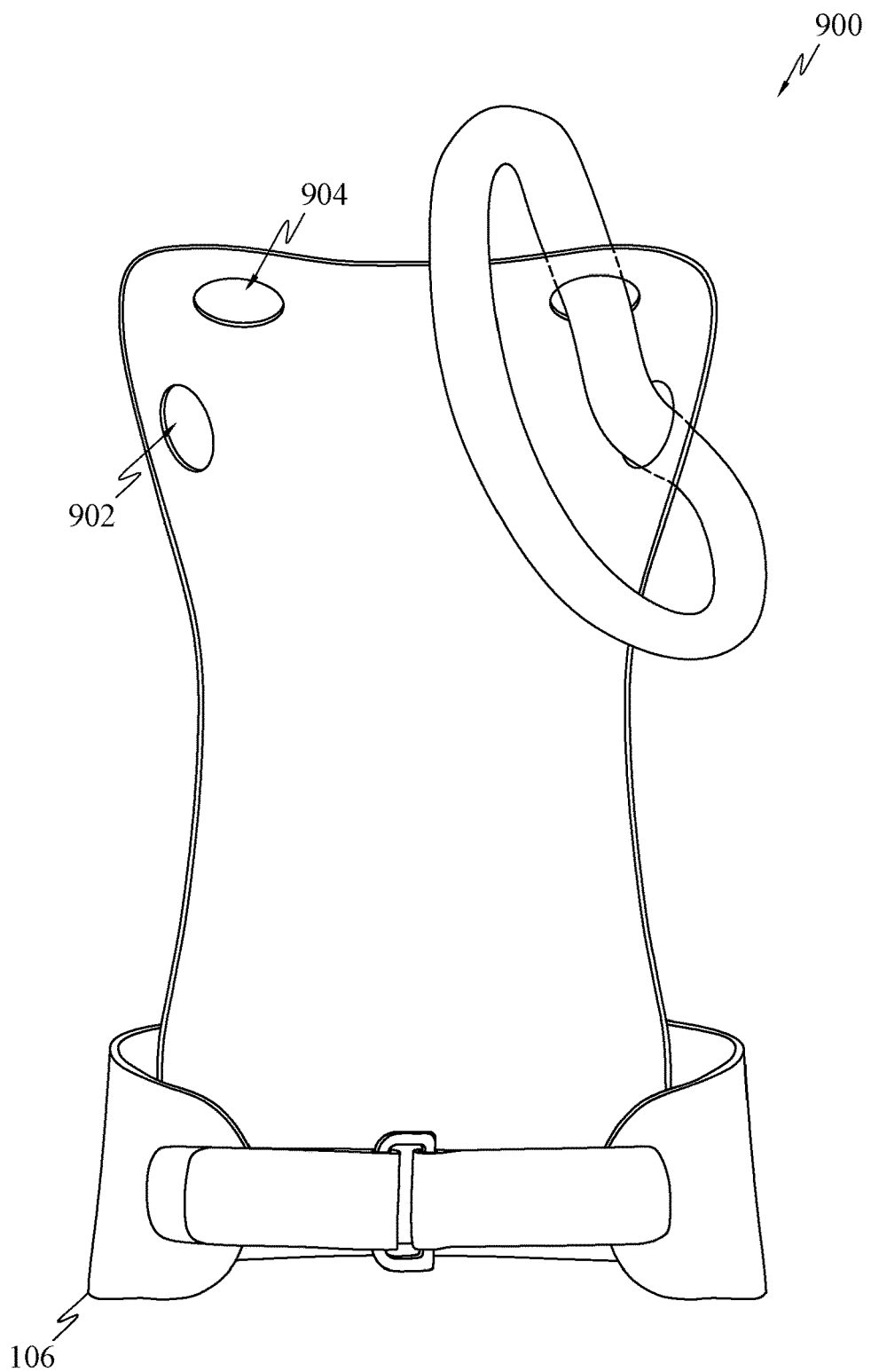
FIG. 9 illustrates a posture correction brace comprising grooves in a first member for connecting a pair of second members to the first member, in accordance with an embodiment.

FIG. 9 illustrates a posture correction brace 900, in accordance with an embodiment. The second member 104 may be connected to the first member in many different ways. For example, the first member 102 may define a first pair of holes 902 and a second pair of holes 904, in the top two corners of the first member 102. Each pair of holes 902 and 904 may be configured to accommodate each second member 104 on each side of the shoulders of the user.

Figure 10:
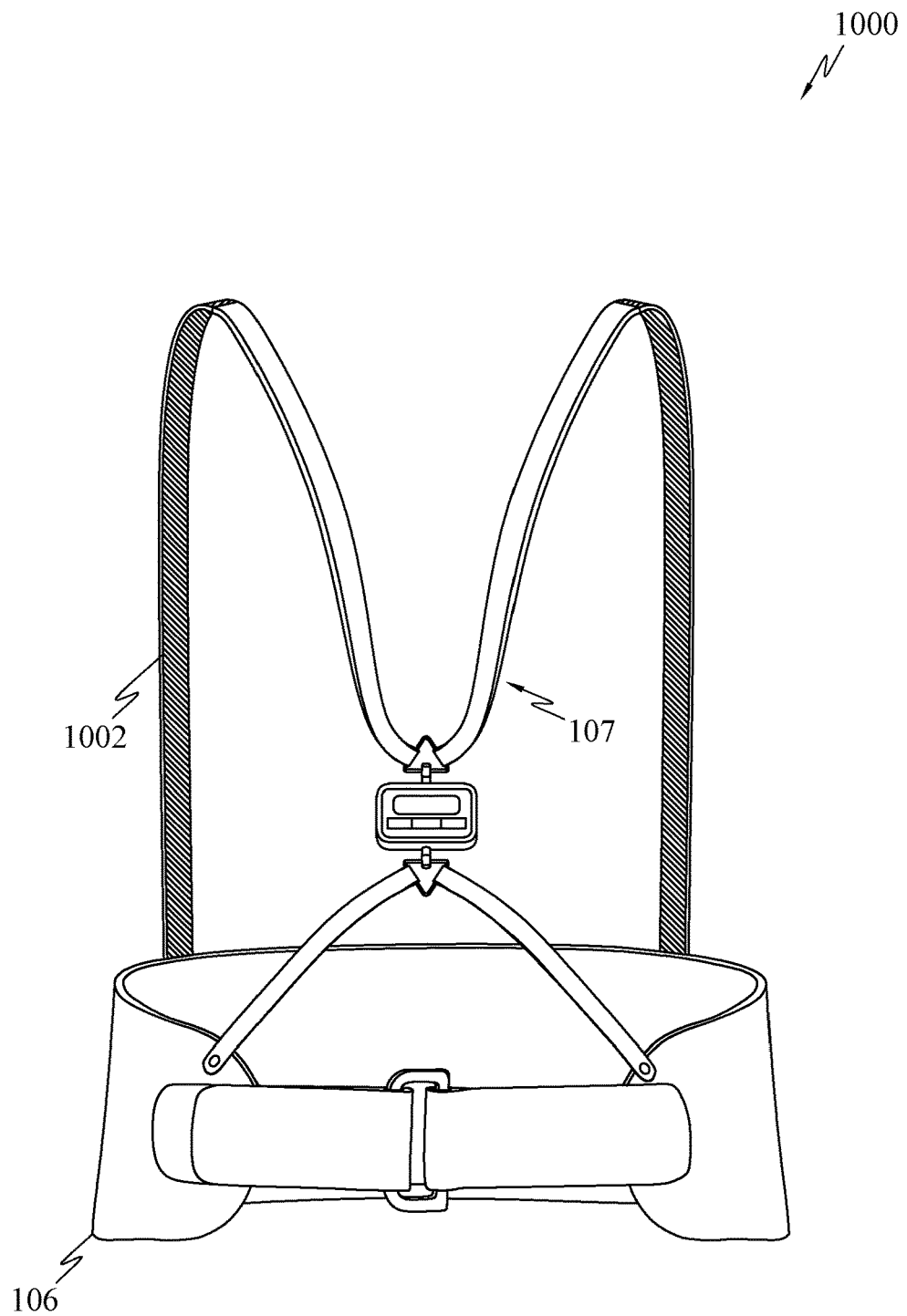
FIG. 10 illustrates a posture correction brace 1000, in accordance with an embodiment.

FIG. 10 illustrates a posture correction brace 1000, in accordance with an embodiment. The first member may be defined as a pair of bands 1002. A first end of each of the pair of bands 1002 may be connected to the third member 106 at the posterior side of the user and a second end of each of the pair of bands 1002 may be connected to the fourth member 107 at the anterior side of the user. Here the principle of resistance in the pair of bands 1002 may remain same as that for the first member 102. As indicated in FIG. 10, the shaded strip 1002 starting at the back from the third member 106, till little over the shoulder in the front may be a non-stretchable or semi-stretchable material to provide the functionality of both first member 102 and second members 104. The pair of bands 1002 may not cover the complete back portion of the user. The pair of bands 1002 may be configured to be positioned parallel to spinal cord of the user on either side of the user in the back portion.

In one embodiment, The non-shaded portion in FIG. 10, depicting the fourth elastic member 107 may be configured to provide the required resistance in the front portion of the user.

Figure 11:
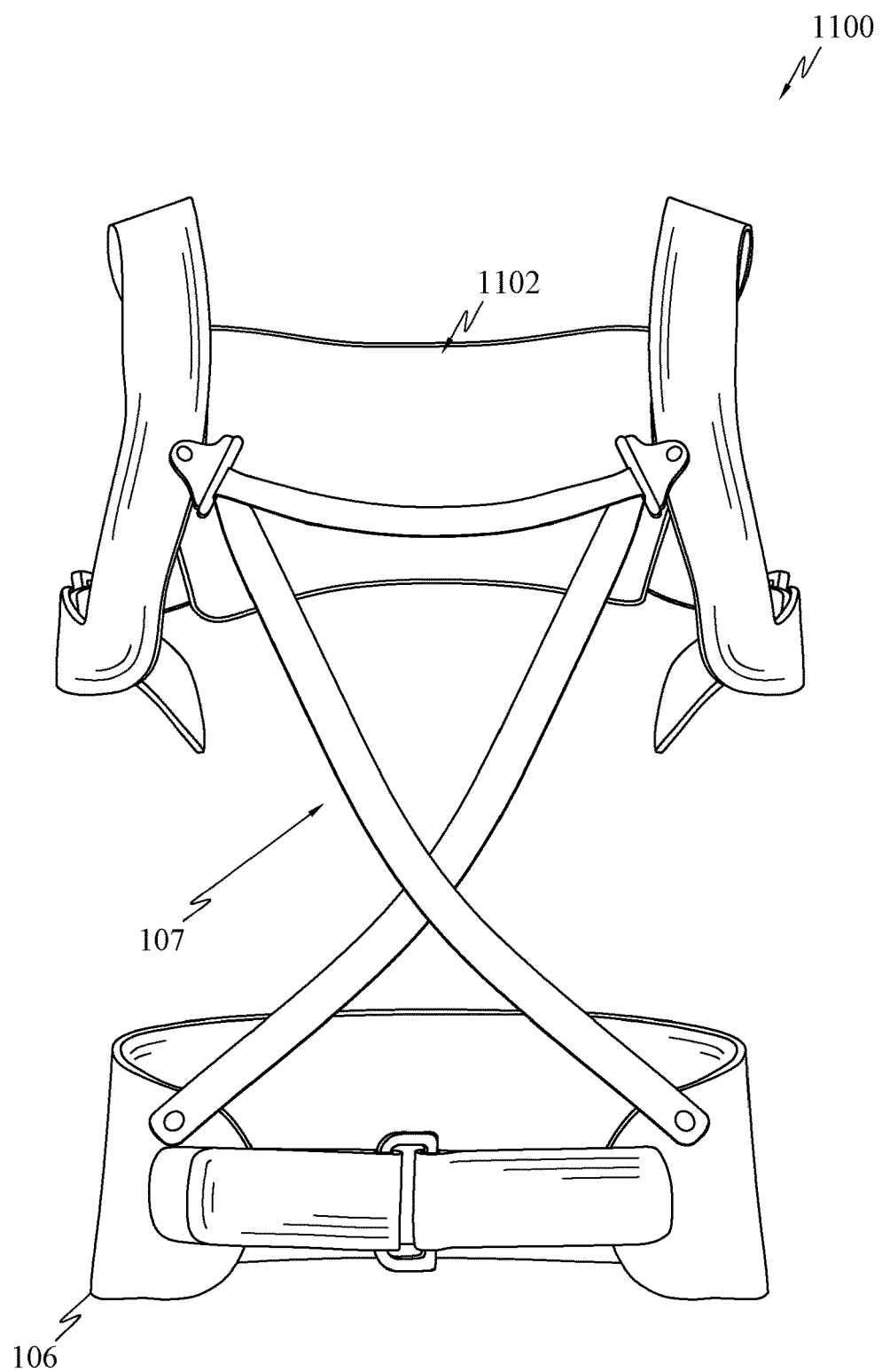
FIG. 11 illustrates a posture correction brace 1100, in accordance with an embodiment.

FIG. 11 illustrates a posture correction brace 1100, in accordance with an embodiment. The brace 1100 may comprise a first member 1102 that may be configured to cover the back portion of the user partially. The first member 1102 may be connected to the pair of second members 104 at the top end of the first member 1102. However, the lower end of the first member 1102 may not be connected to the third member 106. The posture correction brace 1100 may be used for not only correcting the slouch back of the user but also to train the muscles supporting the right posture of the user in order to train the body to maintain the right posture.

Figure 12:
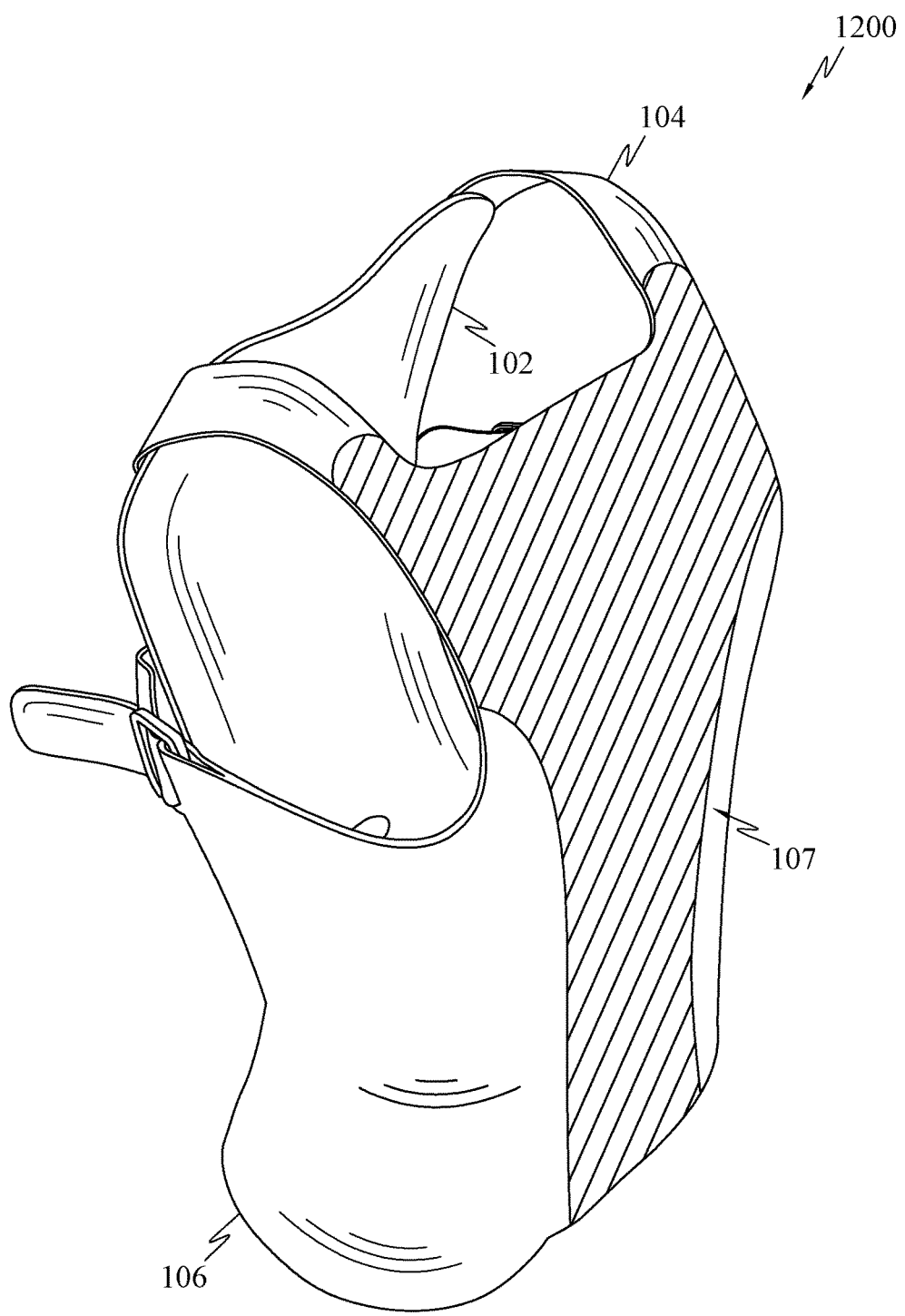
FIG. 12 illustrates a posture correction brace 1200, in accordance with an embodiment.

FIG. 12 illustrates a posture correction brace 1200, in accordance with an embodiment. The brace 1200 may comprise a first member 102. The first member 102 may cover the back portion fully or partially. The first member 102 will be connected to the pair of second members 104 at the top end of the first member 102 while the lower end may or may not be connected to the third member 106 based on whether the first member 102 covers the back portion fully or partially. The fourth elastic member 107 may be in the form of a vest covering the front portion of the user. This fourth elastic member can be made of stretchable fabric including any one of the new technical fabric to provide the required resistance. The upper portion of the vest-shaped fourth member 107 may be connected to the pair of second members 104. The lower portion of the vest-shaped fourth member 107 may be connected to the third member 106 in the front portion of the user. Further, the fourth elastic member 107 may be configured to cover the sides of the user when the first member 102 covers the complete back portion of the user. Like in previous embodiments, 102, 104 and 106 material can be same or different material but would be of the material that is less stretchable than 107.

The fourth elastic member 107 in its various configuration across all variations may be designed to provide resistance that should help in training and strengthening the posture muscles. For better understanding, the variations of the resistance provided by fourth member 107 may be resolved in two components. One component may provide the resistance in a vertical direction while trying to keep the spine straight/erect. The other component may provide the resistance in the horizontal direction that may help the user train and strengthen the shoulder and back muscle to keep the chest pulled, thereby avoid rounding of shoulder or hollowing the chest. Similar effects may be deduced for the diagonal resistance, thus may assist the user to maintain an optimal posture. The optimal posture and amount of resistance may be determined by the user, while the device may help strengthen and training to the muscles to maintain optimal posture by providing proper resistance.

In different embodiments of the brace, there may be joints in the form of clips or buckles incorporated in the embodiments to ease the wearing and removal of the brace by opening or loosening it.

The described embodiments comprise different features, not all of which are required in all embodiments, but the basic tenant of the preferred embodiment can be retained that the resistance may be offered on the front portion of the brace keeping body dynamics in mind while the back portion, shoulder strap and waist band may work as a support/anchor to the resistance providing components.

The various embodiments have been described using detailed descriptions that are provided by way of example and are not intended to limit the scope of the invention. The described embodiments comprise different features, not all of which are required in all embodiments. Some embodiments utilize only some of the features or possible combinations of the features. Many other ramification and variations are possible within the teaching of the embodiments comprising different combinations of features noted in the described embodiments.

It will be appreciated by persons skilled in the art that the various embodiments are not limited by what has been particularly shown and described herein above. Rather the scope of the invention is defined by the claims that follow.

What is claimed is:

1. A posture correction brace, the posture correction brace comprising:
    a first member configured to support at least an upper back portion of a user;
    a pair of second members extending from the superior side of the first member and configured to extend over the shoulders of the user;
    a third member configured to surround a portion of the waist region of the user; and
    a fourth elastic member, wherein the fourth elastic member comprises of a first end and a second end, wherein the first end of the fourth elastic member is connected to a first region of the third member and the second end of the fourth elastic member is connected to a second region of the third member, wherein the fourth elastic member is configured to interface with a mechanism to offer resistance to at least one of staying erect or stretching the chest for keeping the shoulder broad, the mechanism comprising:
    a first swivel coupled to one of the second members; and
    a second swivel coupled to another of the second members, wherein:
        the fourth elastic member extends from the first region and the second region in diagonally opposite direction towards the first swivel and the second swivel, respectively;
        the first swivel is located diagonally opposite to the first region and the second swivel is located diagonally opposite to the second region; and
        a looping path of the fourth elastic member consists of looping through the first swivel and the second swivel to define a horizontal connection extending between the first swivel and the second swivel, thereby between the second members, and a diagonal connection between the second members and the third member.

2. The posture correction brace of claim 1, wherein the posture correction brace comprises:
    a pair of first tension adjusting devices, wherein each of the pair of first tension adjusting devices is coupled to one second member and configured to adjust a tension of the pair of second members.

3. The posture correction brace of claim 1, wherein the posture correction brace comprises:
    a second tension adjusting device coupled to the third member configured to adjust a tension of the third member.

4. The posture correction brace of claim 1, wherein the posture correction brace comprises:
    a third tension adjusting device coupled to the fourth elastic member configured to adjust a tension of the fourth elastic member thereby adjusting a resistance offered by the fourth elastic member.

5. The posture correction brace of claim 1, wherein the posture correction brace comprises a third connector, and wherein the fourth elastic member comprises:
    a thirteenth strap, wherein:
        a first end of the thirteenth strap is connected to the third connector;
        a second end of the thirteenth strap is connected to the first region of the third member, wherein the second end of the thirteenth strap is the first end of the fourth elastic member; and
        the thirteenth strap passes through the first swivel that is disposed diagonally opposite to the first region of the third member with which the second end of the thirteenth strap is coupled; and
    a fourteenth strap, wherein:
        a first end of the fourteenth strap is connected to the third connector;
        a second end of the fourteenth strap is connected to the second region of the third member, wherein the second end of the fourteenth strap is the second end of the fourth elastic member; and
        the fourteenth strap passes through the second swivel that is disposed diagonally opposite to the second region of the third member with which the second end of the fourteenth strap is coupled, wherein the third connector is disposed between at least a portion of the fourth elastic member that connects the pair of second members with each other at the anterior side in the horizontal direction.

6. The posture correction brace of claim 1, wherein the posture correction brace comprises:
    a tension monitoring device configured to:
        monitor the tension in the fourth elastic member; and
        trigger an alarm if the tension in the fourth elastic member is different from a predetermined tension;

the fourth elastic member, wherein the fourth elastic member comprises:

a fifteenth strap, wherein;

a first end of the fifteenth strap is connected to the tension monitoring device;

a second end of the fifteenth strap is connected to the first region of the third member, wherein the second end of the fifteenth strap is the first end of the fourth elastic member; and the fifteenth strap passes through the first swivel that is diagonally opposite to the third member with which the second end of the fifteenth strap is coupled; and a sixteenth strap, wherein:

a first end of the sixteenth strap is connected to the tension monitoring device;

a second end of the sixteenth strap is connected to the second region of the third member, wherein the second end of the sixteenth strap is the second end of the fourth elastic member; and the sixteenth strap passes through the second swivel that is diagonally opposite to the third member with which the second end of the sixteenth strap is coupled, wherein, the tension monitoring device is disposed between at least a portion of the fourth elastic member that connects the pair of second members with each other at the anterior side in the horizontal direction; and the tension monitoring device is connected to the fifteenth strap and the sixteenth strap via additional swivels.

7. The posture correction brace of claim 1, wherein:
the first member is made using a first material;
each of the pair of second members is made using a second material;
the third member is made using a third material; and
the fourth elastic member is made using a fourth material.

8. The posture correction brace of claim 1, wherein:
the first member is less stretchable than the second member, third member and the fourth elastic member;
the third member is less than or as stretchable as the second member; and
the fourth elastic member is more stretchable than the first member, second member and the third member.

9. The posture correction brace of claim 1, wherein the first member is configured to partially cover the back portion of the user.

10. The posture correction brace of claim 1, wherein the first member, the second member and the third member are coupled with each other by a stitch connection.

11. The posture correction brace of claim 1, wherein the first member, the second member and the third member are coupled with each other by a button connection.

12. The posture correction brace of claim 1, wherein:
the first member comprises of a lower edge;
the third member comprises of an upper edge facing the lower edge of the first member; and
the first member and the third member are spaced apart, wherein a gap is defined between the lower edge of the first member and the upper edge of the third member, when the posture correction brace is worn by the user.

* * * * *